(12) United States Patent
O'Connor et al.

(10) Patent No.: US 6,244,753 B1
(45) Date of Patent: *Jun. 12, 2001

(54) CHEMICAL ANALYZER OPTICAL PROBE AND METHOD OF MANUFACTURING SAME

(75) Inventors: Eamon O'Connor, Limerick (IE); John M. Jarvis, Bloomington, MN (US); John J. O'Donnell, Ennis (IE)

(73) Assignee: Rosemount Analytical, Inc., LaHarba, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 17 days.

(21) Appl. No.: 09/038,350

(22) Filed: Mar. 11, 1998

Related U.S. Application Data
(60) Provisional application No. 60/040,769, filed on Mar. 14, 1997.

(51) Int. Cl.[7] .............................. G02B 6/00; G02B 6/38; G02B 6/36
(52) U.S. Cl. ............................... 385/75; 385/12; 385/26; 385/77; 385/78
(58) Field of Search ............................... 385/75, 12, 78, 385/76, 77

(56) References Cited

U.S. PATENT DOCUMENTS

| | | | |
|---|---|---|---|
| 3,985,508 | 10/1976 | Williams | 23/253 R |
| 4,127,329 | 11/1978 | Chang et al. | 356/301 |
| 4,648,714 | 3/1987 | Benner et al. | 356/301 |
| 4,953,976 | 9/1990 | Adler-Golden et al. | 356/301 |
| 5,112,127 | 5/1992 | Carrabba et al. | 356/301 |
| 5,455,673 | 10/1995 | Alsmeyer et al. | 356/301 |
| 5,534,997 | 7/1996 | Schrader | 356/301 |
| 5,678,751 | 10/1997 | Buchanan et al. | 228/124.6 |
| 5,710,626 | 1/1998 | O'Rourke et al. | 356/301 |
| 5,963,319 | * 10/1999 | Jarvis et al. | 356/301 |
| 5,986,755 | * 11/1999 | Ornitz et al. | 356/301 |
| 6,008,488 | * 12/1999 | Jarvis et al. | 250/227.23 |

FOREIGN PATENT DOCUMENTS 0 405 752 A2  1/1991  (EP) .

OTHER PUBLICATIONS

"Fiber Raman background study and its application in setting up optical fiber Raman probes", by Jiayang Ma and Ying–Sing Li, Applied Optics, May 20, 1996, vol. 35, No. 15, pp. 2527–2533.

* cited by examiner

*Primary Examiner*—Frank G. Font
*Assistant Examiner*—Armando Rodriguez
(74) *Attorney, Agent, or Firm*—Westman, Champlin & Kelly, P.A.

(57) ABSTRACT

An instrument that analyzes chemical properties of a specimen includes a probe that is used in place on the specimen for spectroscopic analysis. The probe has a probe body with a proximal end and a distal end, and a first optical fiber extends from the proximal to the distal ends. A temperature sensor is included in the probe body and is used so insure that the probe does not exceed a rated temperature limit or to monitor specimen temperature while, simultaneously, chemical composition information of the specimen is transmitted by the optical fiber. The probe can be inserted into a container holding the specimen and can yield both temperature and chemical composition information. The probe includes a plurality of metal coated fibers with the distal ends of the fibers positioned inside a bore in the probe. Braze material is placed on the probe near the bore and the braze material is then brazed to the metal coating on the ends of the fiber.

13 Claims, 5 Drawing Sheets

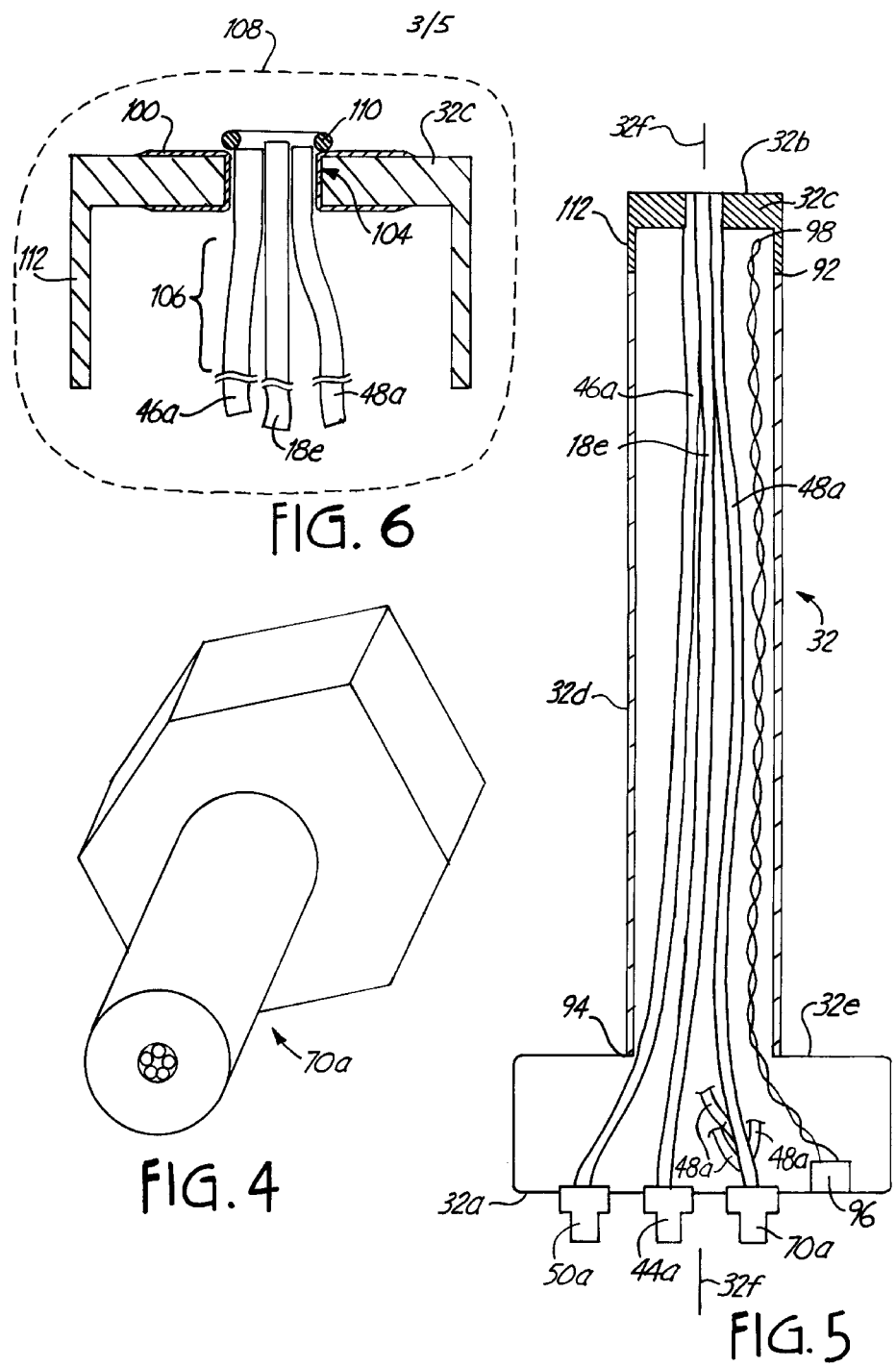

US 6,244,753 B1

CHEMICAL ANALYZER OPTICAL PROBE AND METHOD OF MANUFACTURING SAME

CROSS REFERENCE TO RELATED APPLICATIONS

This application claims priority from Provisional Application Ser. No. 60/040,769, entitled CHEMICAL ANALYZER OPTICAL PROBE AND METHOD OF MANUFACTURING SAME, filed Mar. 14, 1997 by O'Conner et al. This application is related to the following copending applications which are incorporated herein by reference and filed on even date herewith: "Improved Rayleigh Backscatter Control Apparatus and Method" (Ser. No. 09/038,348 filed Mar. 11, 1998), "Improved Low Noise Raman Analyzer System" (Ser. No. 09/038,438 filed Mar. 11, 1998), and "Chemical Analyzer With Free Space Communication Link" (Ser. No. 09/038,438 filed Mar. 11, 1998), all having common ownership and inventorship with the present application; and "Raleigh Backscatter Control Apparatus and Method" (Ser. No. 08/947,816 filed Oct. 9, 1997;), and "Method For Standardizing Raman Spectrometers To Obtain Stable And Transferable Calibrations" (Ser. No. 08/947,689 filed on Oct. 9, 1999;), assigned to Eastman Chemical Co.

BACKGROUND OF THE INVENTION

The present invention relates to instruments that analyze chemical properties of a specimen using optical means. More specifically, the invention relates to probe design and construction for such instruments. The invention has particular application to such instruments that detect Raman-scattered light from the specimen.

BRIEF SUMMARY OF THE INVENTION

One aspect of the invention relates to a novel in situ probe for spectroscopic analysis. The probe has a probe body with a distal end and a proximal end, and a first optical fiber extending from the proximal to the distal end. Advantageously, a temperature sensor is included in the probe body and disposed proximate the distal end. The temperature sensor can be used for example to ensure that the probe does not exceed a rated temperature limit, or to monitor a specimen temperature while simultaneously analyzing a chemical composition of the specimen via the optical fiber. Hence, one insertion point into a container holding the specimen can yield both a temperature and chemical composition measurement. Preferred embodiments include additional optical fibers disposed in the probe body, and connectors held at the proximal end of the probe. A preferred temperature sensor is a thermocouple.

Another aspect of the invention relates to a method of constructing a fiber optic probe. A plurality of metal-coated fibers having proximal and distal ends are provided, and the distal ends are positioned inside a bore in the probe end. The probe end has a metal coating. Braze material is placed on the probe end near the bore, and the assembly is heated in a vacuum oven. In a preferred embodiment an anti-wicking agent is applied to the fibers in a zone near the distal ends prior to heating. Also in the preferred embodiment the metal coating on the probe end is limited to a vicinity in, or in and around, the bore. The braze material is preferably a binary alloy of silver and copper.

BRIEF DESCRIPTION OF THE DRAWINGS

FIG. 4 is a perspective end view of a male fiber connector showing an arrangement of optical fibers at the connector end as used in the analyzer of FIG. 1;

FIG. 5 is a partially sectional view of a preferred optical probe useable with the analyzer of FIG. 1;

FIG. 6 is a sectional view of a distal end of the probe of FIG. 5 during probe fabrication;

For convenience, items in the figures having the same reference symbol are the same or serve the same or a similar function.

DETAILED DESCRIPTION OF THE PREFERRED EMBODIMENTS

As used herein, "optic" (al) and "light" refer to electromagnetic radiation, whether or not visible to the human eye.

Figure 1:
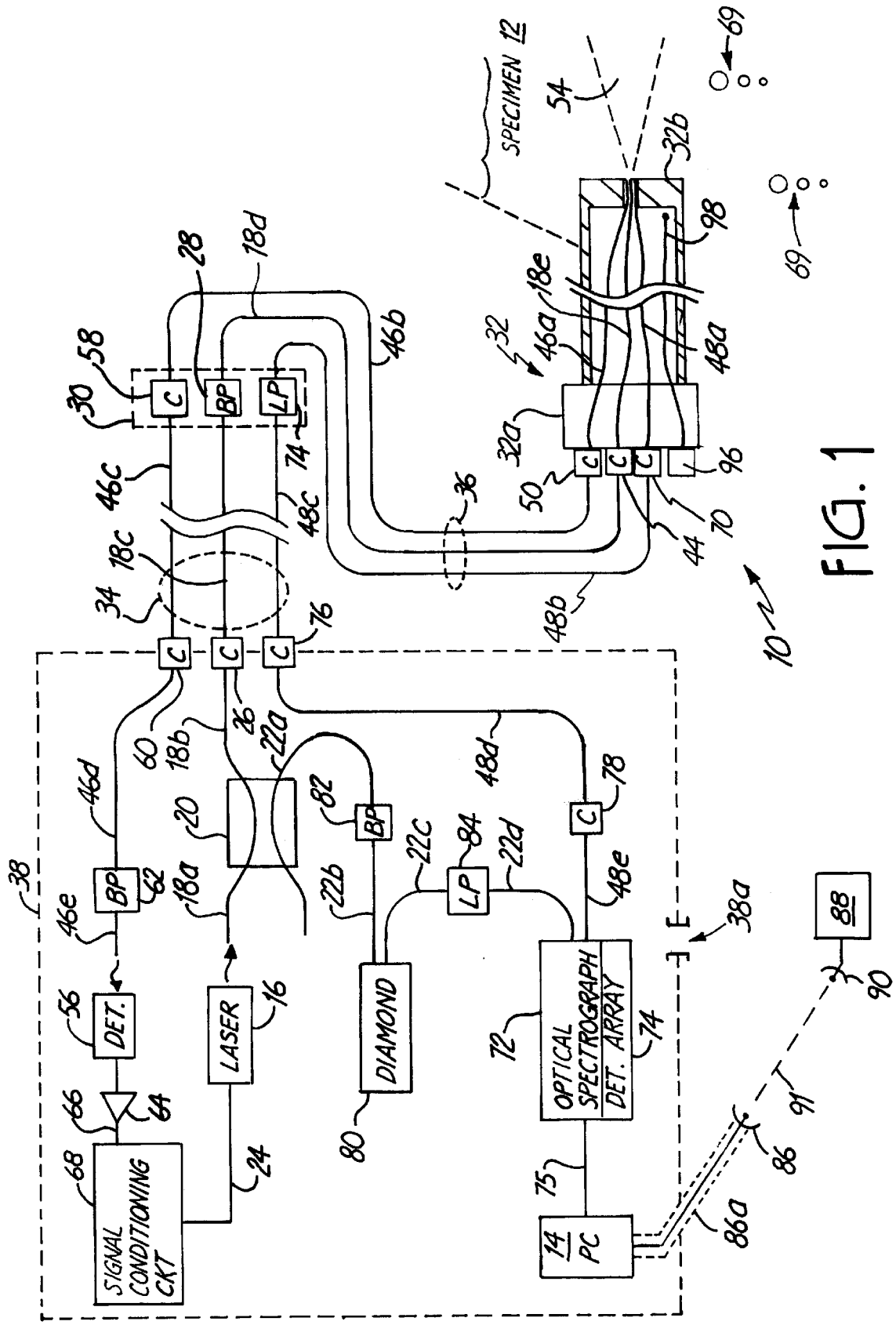
FIG. 1 shows a system diagram of a preferred chemical analyzer in accordance with an aspect of the invention.

FIG. 1 shows a preferred analyzer 10 that evaluates a specimen of interest 12 and provides on a computer 14 or other suitable output medium an analyzer output indicative of the presence or amount of one or more chemical constituents of the specimen. The analyzer 10 illuminates the specimen 12 with narrow-band light, collects backscattered light from the specimen, optically isolates a Raman scattering component from the backscattered light, and evaluates the Raman scattering component to calculate the analyzer output. Simultaneously, the analyzer isolates a Rayleigh scattering component from the backscattered light. If the Rayleigh scattering component falls below a threshold level, which may result for example from disconnecting a fiber connector or withdrawing the probe from the specimen, the narrow-band light illumination is shut off. This shut off technique is most effective in specimens such as liquids that have significantly higher Rayleigh scattering levels than that of gasses such as air.

A diode laser 16 launches essentially monochromatic, narrow-band light into a fiber 18a of a 2-by-2 beamsplitter 20. A wavelength of about 810 nanometers (nm) for the narrow-band light has been found satisfactory. Shorter wavelengths increase the amount of Raman scattering, but may also produce unwanted fluorescence in some specimens; longer wavelengths are less likely to produce fluorescence but yield a lower Raman signal. In practice, a diode laser having a wavelength between about 750 and 850 nm is preferred. The selected wavelength should not however coincide with an absorption line of the specimen 12, if maximum Raman scattering levels are desired. The laser can have a multimode output and be capable of emitting 700 mW to 1.2 W of optical power during analyzer operation. Laser 16 also includes a driver circuit with a control input at line 24, and a temperature control circuit if the laser source is a diode laser. The control input of laser 16 controls the amount or intensity of narrow band light injected into fiber 18a.

Beamsplitter 20 divides the laser light launched into fiber 18a between fibers 18b, 22a, preferably in equal amounts although other ratios are also contemplated. The narrow band light passes from fiber 18b to a fiber 18c via a connector pair 26. Connector pair 26 includes a male connector end holding each fiber end, the connector ends facing each other inside an alignment bushing. SMA-type connector pairs are preferred for robustness and ease of modification to nonstandard bore sizes, but other known styles such as ST or FC are also contemplated. Fiber 18c connects to a bandpass filter 28 in a fiber termination/filter module 30. Laser light passes through filter 28 to a fiber 18d, which carries the light to a probe 32 adapted to contact the specimen 12. Fibers 18c,18d are preferably part of armored cable assemblies 34,36 respectively.

The analyzer 10 is preferably arranged as a main analyzer unit 38 situated in a control room (or other suitable location that can provide the necessary electrical power), a probe 32 located at the specimen, and the termination/filter module 30 located near the probe. Main analyzer unit 38 is preferably housed in an intrinsically safe enclosure, configured with an industry standard Z-purge capability at a port 38a that maintains a positive air pressure inside unit 38 relative to its surroundings. Armored fiber cable assemblies 34,36 connect unit 38 to module 30, and module 30 to probe 32, respectively. Cable assembly 34 can be tens or hundreds of meters long.

Optical fiber can itself generate Raman scattering and/or fluorescence (hereinafter, "spurious light signals") from laser light passing through it, which if detected can be confused with Raman scattering from the specimen. The spurious light signals are a function of the fiber properties (most importantly its length, but also including core material, cladding material, and buffer layer material), and generally have wavelengths longer than the laser wavelength. Therefore, bandpass filter 28 is provided in the termination/filter module 30, and module 30 is located as close to the probe as possible to minimize fiber 18d length and thus minimize any spurious light signals generated in fiber 18d. In a benign environment, the cable assembly 36 (including fiber 18d) can be eliminated and the filter 28 and the other filter (74, discussed below) can be mounted directly on the proximal end of the probe 32. However, in many practical applications the temperature or change in temperature encountered even at the proximal end of the probe can have adverse effects on filter performance. Hence, module 30 mounted away from probe 30 provides a more stable temperature environment for the filters 28,74. Bandpass filter 28 blocks the spurious light signals originating in fibers 18a, 18b, 18c, from reaching fiber 18d, but passes narrow band light from laser 16.

Spurious light signals can be further reduced by using silica-based fiber having an inert metal buffer layer such as gold. Such fibers have significantly lower spurious light signals than similar fibers having a polymer-based buffer layer such as polyimide The relatively high cost of the metal-coated fibers however can make it impractical to use them exclusively in analyzer 10, depending on the distances involved. Instead, the use of filters 28,74 permits lower cost, polymer-based fibers to be used between the main analyzer unit 38 and the filters, and the preferred gold-coated fibers to be used in probe 32 and between probe 32 and the filters.

Figure 2:
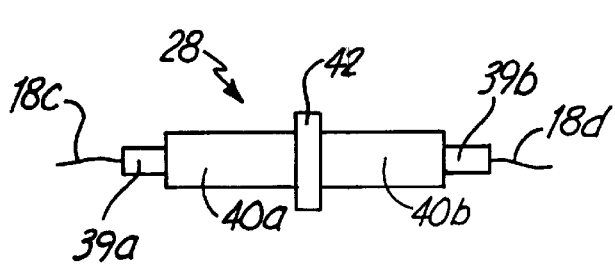
FIG. 2 depicts chief components of a preferred optical filter used in the analyzer of FIG. 1.

A preferred embodiment of filter 28 is depicted in FIG. 2. Male fiber connectors 39a,39b hold the ends of fibers 18c,18d against 0.25-pitch gradient index (GRIN) lenses 40a,40b respectively. A filter 42 sandwiched between lenses 40a,40b provides the desired spectral filtering characteristics. Filter 42 preferably comprises an interference-type filter.

Figure 3:
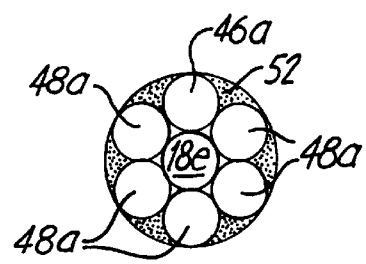
FIG. 3 is an enlarged end view of optical fibers in the probe shown in FIGS. 1 and 5.

Turning again to FIG. 1, fiber 18d releasably connects to probe 32 by a connector pair 44 located at a proximal end 32a of probe 32 and passes narrow band light to a fiber 18e that extends from connector pair 44 to a distal end 32b of probe 32. Also housed in probe 32 are a fiber 46a and a group of five fibers 48a. The line representing fibers 48a, and some other lines in FIG. 1, are shown thickened to indicate multiple optical fibers in the preferred embodiment. Fiber 46a connects to a connector pair 50 at proximal end 32a, and at distal end 32b is brazed or otherwise held in position together with fibers 18e and 48a. At end 32b, the fibers are polished to a mirror finish and arranged as shown in FIG. 3. A braze material 52 holds the fiber ends in place and hermetically seals the probe at end 32b. The probe design and construction is discussed further below.

Narrow band light exits fiber 18e and illuminates specimen 12 in a detection zone 54 defined by the numerical aperture of fiber 18e. The surrounding six fibers (46a and 48a) collect some of the backscattered light, which will include a relatively strong Rayleigh component (same wavelength as the narrow band light) and a relatively weak Raman component (longer wavelength than the narrow band light). As will be seen, the preferred analyzer 10 uses the multiple fibers 48a to boost the detected Raman component and the single fiber 46a to sense the Rayleigh component for continuity.

Backscattered light traveling down fiber 46a is directed to a detector 56 via fibers 46b–e, connector pairs 58,60, and a bandpass filter 62. Filter 62 passes the narrow band light wavelength and is substantially identical to previously described filter 28. The purpose of filter 62 is to prevent sunlight, room light, or any other extraneous light collected by fiber 46a from being mistaken for Rayleigh backscattered light. Filter 62 also has the effect of preventing the weaker Raman component, if present, from reaching detector 56. An amplifier 64 couples to detector 56 to provide an amplified detector output on line 66.

Advantageously, the detector 56 output, representative of the Rayleigh scattering component, is fed back through a signal conditioning circuit 68 to the laser control input at line 24. Circuit 68 compares the detector output on line 66 with a predefined threshold. If the detector output is above the threshold, indicating that the analyzer optical system is intact, circuit 68 provides an output on line 24 that maintains laser 16 at its normal, relatively high, output level. If on the other hand the detector output is below the threshold, indicating a fiber disconnection or break, or removal of the probe from the specimen, circuit 68 provides an output on line 24 that shuts off laser 16 or at least controls it to a lower intensity level. This lower intensity level can be set such that the light intensity emitted from probe fiber 18e, and preferably from fiber 18b, is within BSI/EN 60825-1 class 1 operation (i.e., nonhazardous direct viewing). In this way, analyzer 10 can operate with high laser light levels during normal operation and automatically shut down if a discontinuity is sensed by detector 56, thereby avoiding hazardous viewing by an operator.

Several enhancements to the basic shut-down technique are also provided by signal conditioning circuit 68. One enhancement is the ability to discriminate between transient losses in the Rayleigh scattering component, such as may be caused by small bubbles 69 of air or other gas passing through the detection zone 54, and longer lived losses in the signal which may result from fiber disconnection or break, or a withdrawal of probe 32 from the specimen. The circuit 68 continues driving laser 16 at its high operational intensity level in the presence of the truly transient losses, but shuts the laser down to the lower intensity level for the longer-lived losses. This discrimination function prevents unnecessary and annoying shutdowns during operation of analyzer 10. Another enhancement involves periodically interrogating the laser 16 after a shutdown has occurred, or at startup, so that if system integrity is restored the analyzer 10 will automatically return to normal operation (i.e., high laser intensity level). These capabilities of circuit 68 are described in more detail below.

Turning again to probe 32 in FIG. 1, fibers 48a are unsupported in probe 32 except at distal end 32b, where they are arranged around the emitting fiber as shown in FIG. 3, and at the proximal end 32a, where they are bundled together at a connector pair 70. One of the male connector ends 70a of pair 70 holds the five fibers 48a as shown in the perspective end view of FIG. 4. The other male connector end of pair 70 holds a single fiber 48b in alignment with the fibers 48a, where fiber 48b has a diameter sufficiently large to capture light emitted from all of the fibers 48a. For example, if fibers 48 are 100 $\mu$m (core diameter), fiber 48b can be about 300 $\mu$m (core dia.). This arrangement greatly simplifies analyzer 10 interconnections: rather than five separate fibers, connector pairs, and filters connecting the Raman pickup fiber channel from the probe 32 to the main analyzer unit 38, only one-fifth of those components are required by using a large fiber to collect light from fibers 48. Backscattered light is carried by fiber 48b to the entrance slit of an optical spectrograph 72 via a long pass filter 74, fibers 48c–e, and connector pairs 76,78. Long pass filter 74 has the same construction as the bandpass filter shown in FIG. 2 except that the filter element 42 is fabricated to block the narrow band light of laser 16 and pass longer wavelengths. Preferably the spectral transmission of filter 74 is less than $10^{-6}$ at the laser wavelength 810 nm and rises to half of its peak transmittance (70% typ. peak trans.) at about 833 $\mu$m. As discussed, fiber termination/filter module 30 is mounted close to probe 32 to keep fiber 48b short (generally no more than a few, and preferably <1 meter), so that no spurious light signals can be produced by Rayleigh backscattered light in fiber 48b. Filter 74 blocks any Rayleigh backscattered light from reaching fibers 48c–e. Fiber 48b preferably has a metal (gold)-buffer layer.

Fibers 18a–e, 46a, 48a, 48e, and 22a–d are preferably relatively small diameter (e.g. 100 $\mu$m core) fibers, while fibers 48b–d are preferably relatively large diameter (e.g. 300 $\mu$m core) fibers. Fibers 46b–e can be either small or large diameter, but preferably are no smaller than fiber 46a. All can be graded-index or, preferably, step-index for increased light levels. Fibers 48e are held at connector pair 78 in a substantially circular pattern (similar to FIG. 4) for optimal coupling to fiber 48d, while at the entrance slit to spectrograph 72 they are held in a linear array. Fibers 18d, 18e, 46a, 48a, and 48b all have inert metal buffer layers, preferably gold.

A diamond reference 80 is provided in main analyzer unit 38. Fibers 18a, 22a,22b carry narrow band light from laser 16 to the surface of diamond 80. Bandpass filter 82, substantially identical to filters 28 and 62, blocks fiber-generated Raman scattering. Six fibers 22c surround fiber 22b at the diamond surface (similar to FIG. 3) to capture backscattered light from diamond 80. A longpass filter 84, substantially identical to filter 74, blocks Rayleigh scattered light from fibers 22d. Fibers 22d, six in number, are arranged circularly at filter 84 and linearly at the spectrograph 72 entrance slit.

The linear arrays of fibers 22d and 48e are arranged colinearly, one abutting the other, at the entrance slit to spectrograph 72. Spectrograph 72 is preferably equivalent to model SP-150 available from Acton Research Corp., and has a ruled grating with 400 grooves/mm and blazed at 750 nm. A detector array 74, preferably 750 pixels wide by 240 pixels high, intercepts and simultaneously monitors the spatially separated Raman scattered light spectra from the specimen 12 and from the diamond reference 80. The output from detector array 74 is fed to computer 14 over a line 75. Signal processing software residing in computer 14 is used to produce a standardized Raman spectrum of the specimen (see copending application of Eastman Chemical Co. entitled "Method For Standardizing Raman Spectrometers To Obtain Stable And Transferable Calibrations", filed Oct. 9, 1999, now U.S. Pat. No. 5,550,623, incorporated herein by reference) using the diamond Raman spectrum. Pattern recognition software also residing in computer 14 calculates the chemical composition of specimen 12 from the standardized Raman spectrum of the specimen and calibration training data. Such pattern recognition software is available from Galactic Industries, Boston, Mass.

As previously mentioned, main analyzer unit 38 is preferably intrinsically safe. Although computers having intrinsically safe keyboards and monitors are commercially available, there are significant difficulties in providing a convenient and aesthetic user interface using these components. Therefore, computer 14 is preferably equipped with a transceiver 86 such as an antenna or an infrared transmitter/receiver. A user can send instructions to and receive information from computer 14 using a second device such as a laptop computer 88 equipped with a similar transceiver 90. Such communication preferably occurs over a wireless, fiberless free space path 91, allowing the user to freely move from place to place with computer 88 and permitting greater flexibility and choice in a mounting location for main analyzer unit 38. Preferred transceivers 86,90 are commercially available radio LAN cards for desktop or laptop computers, for example the WAVELAN card available from AT&T Lucent Technologies, designed to interface to a standard PC/MCIA slot or Industry Standard Architecture (ISA) bus slot. Transceiver 86 is depicted in FIG. 1 as such an antenna device, that partially extends out of the housing of unit 38 and connects to computer 14 by a coax line 86a. The transceiver can also be an infrared emitter/receiver disposed inside the housing of unit 38 behind a window. Computer 88 has a keyboard and a mouse that are used to send queries and commands to computer 14. Computer 88 also has a display to graph or otherwise show the analyzer output data transmitted from computer 14. With this arrangement, computer 14 is preferably equipped with neither a display screen, a keyboard, nor a mouse, to satisfy intrinsic safety requirements as well as to reduce the size, weight, and electrical requirements of main analyzer unit 38.

Probe 32 is described in more detail in connection with FIGS. 5 and 6, together with previously discussed FIGS. 1, 3, and 4. Probe 32 preferably has a probe body with three main components: a terminus 32c, a shank 32d, and a connector housing 32e, all made of 316 stainless steel or other suitable inert materials capable of withstanding several hundred degree C temperatures, such as Hastelloy C. Terminus 32c, shank 32d, and housing 32e are rotationally symmetric about a probe axis 32f, and are connected by braze joints 92,94 as shown. The outer diameter of terminus 32c, braze joint 92, and shank 32d is polished to a smooth finish (0.25 in. dia.) to permit sealing with a ferrule inside the bore of a standard pipe fitting, such as those available from Swagelok Corp., or the bore of some other container that holds specimen 12.

Fibers 18e, 46a, and 48a (only one of which is shown in its entirety in FIGS. 5 and 6 for simplicity) extend from their respective male connector ends 44a, 50a, and 70a at proximal probe end 32a to distal end 32b. Each of the fibers are step-index, with silica or doped silica core/cladding, and have a thin outer buffer layer of gold, nickel, or other inert metal along their entire length. Male connector ends 50a, 44a, and 70a are fixed to connector housing 32e to permit probe 32 to be conveniently disconnected and reconnected to cable assembly 36 for ease of installation and servicing. Also affixed to housing 32e is a connector 96 for a temperature sensor 98 included in probe 32. Temperature sensor 98 is preferably disposed proximate distal end 32b for diagnostic purposes to ensure that probe 32 does not exceed its rated temperature. Alternately, the output of sensor 98 can be used as a rough indication of the specimen temperature, whereupon probe 32 takes on a dual role as a fiber optic chemical analysis probe and a specimen thermometer. Although known fiber optic temperature sensors can be used for sensor 98, electrical sensors are preferable for their simplicity, and most preferable is a thermocouple (e.g. type K) for its low-cost and reliability. The output of sensor 98 can be monitored with a portable, hand-held device coupled directly to connector 96, or with computer 14, in which case an additional channel such as a twisted wire pair can be included in cable assemblies 36,34.

The procedure for brazing fibers 46a, 18e,48a into the stainless steel terminus 32c will now be described. To enhance adhesion, terminus 32c is plated with gold 100 or other metal matching the metal buffer layer of the fibers. The gold plating extends inside a bore 104 and in the vicinity thereof, but preferably is removed from or not provided on the remaining surfaces of terminus 32c. This is to keep molten braze material in the vicinity of bore 104 during fabrication, preventing it from spreading over the entire terminus 32c. An anti-wicking agent or stop-flow substance, preferably a suspension of magnesium hydroxide in water, is applied to each of the fibers in a zone indicated generally at 106 prior to brazing. Zone 106 approaches but does not touch the distal portion of the fibers that extend into bore 104. The anti-wicking agent inhibits the flow of molten braze material along the fibers substantially beyond bore 104. With the fibers and terminus 32c so prepared, the assembly is positioned in a vacuum oven 108 as shown in FIG. 6, with a small ring or loop of solid braze material 110 resting on top of terminus 32c at or near bore 104. Preferred braze materials for platings 100 made of gold are cadmium-free varieties; widely available braze type (AWS) BAg-8, a binary alloy composed of about 72% silver and 28% copper, is most preferable. The vacuum oven 108 is then heated to a temperature sufficient to melt braze material 110. By preparing the fibers and terminus 32 as described, the molten braze material does not run out of but rather tends to stay in and around the vicinity of bore 104, wicking between the fibers and filling the spaces between them. Upon cooling, the braze material forms a solid hermetic seal within bore 104, uniformly filling the inter-fibral spaces inside bore 104 with few or no voids (see FIG. 3).

As final fabrication steps, a sleeve 112 of terminus 32c is brazed to shank 32d using localized heating, and shank 32d is then brazed to connector housing 32e also using localized heating. The sleeve 112 partially isolates the brazed fibers in bore 104 from heat generated during brazing of terminus 32c to shank 32d. Braze material BAg-8 is used for all braze joints. The fiber ends are polished to a flat, mirror-smooth finish at distal end 32b. Lastly, the other fiber ends are potted into the male connector ends, which connector ends are also brazed to connector housing 32e at proximal end 32a.

Figure 7:
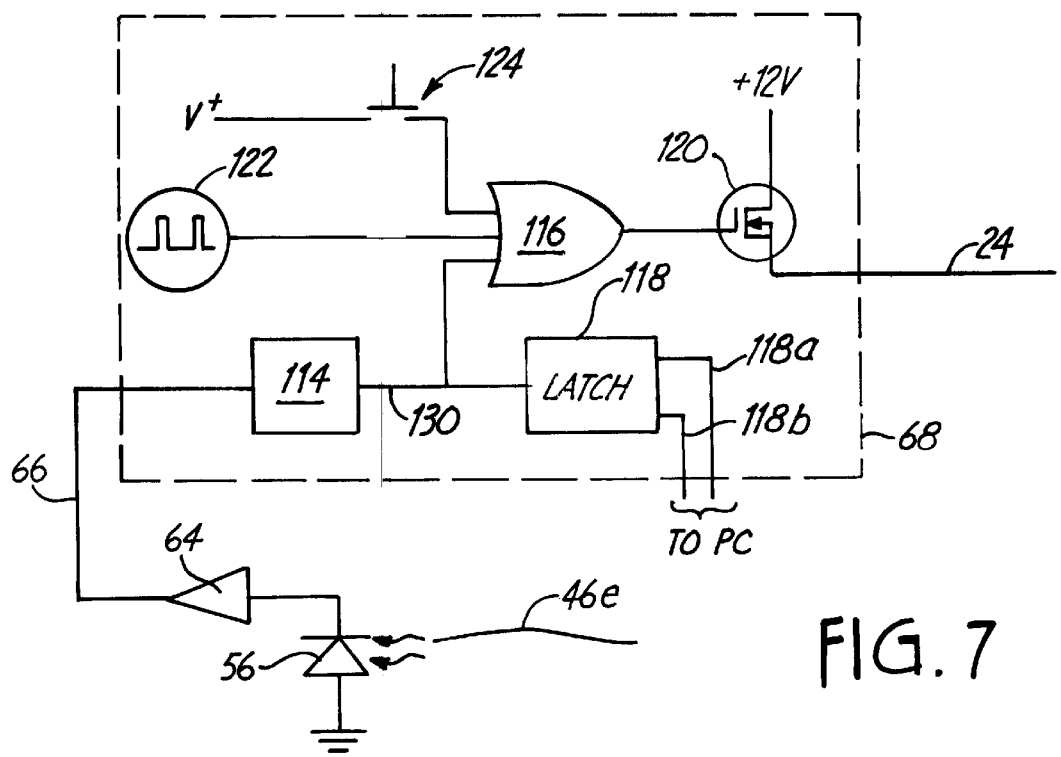
FIG. 7 is a block schematic of a preferred signal conditioning circuit useable with the analyzer of FIG. 1.

FIG. 7 depicts in block schematic form a preferred signal conditioning circuit 68. Circuit 68 receives on line 66 the amplified detector output, representative of the Rayleigh scattering component from specimen 12, and provides on line 24 an output that controls a light output level of laser 16. A comparator/asymmetric discriminator circuit 114 compares the amplified detector output to an adjustable internal threshold. The threshold is adjusted according to the desired laser operational output level, fiber attenuation losses, filter and connector pair losses, and specimen scattering characteristics, to a level less than an output level on line 66 for a fully intact system with the probe contacting the specimen, and greater than a lower output level corresponding to the amount of Rayleigh scattered light received when the probe is withdrawn from the specimen and pointed into the air, or when one of the fiber connector pairs is uncoupled. The output of circuit 114 feeds into an OR gate 116 and a latch 118 as shown. OR gate 116 in turn drives a FET transistor 120 which connects directly or through one or more buffer amplifiers if desired to line 24. Thus, as long as analyzer 10 is intact and probe 32 is disposed in the specimen, the signal on line 66 will be higher than the threshold level, the output of circuit 114 will be "HI", the output of OR gate 116 will be "HI", turning transistor 120 "ON" to couple the +12V voltage to line 24, thereby maintaining laser 16 at its high operational output intensity. If the probe 32 is withdrawn from the specimen, however, the output of circuit 114 will go "LO", as will OR gate 116, turning off transistor 120 and forcing laser 16 to a lower (preferably zero) intensity level.

Circuit 114 also preferably performs a discrimination function against transient losses of the detected Rayleigh scattering component. This function is described in connection with FIG. 8.

The latch 118 is provided so that computer 14 can monitor the activity of circuit 114. An output line 118a conveys the status of the latch to the computer, and a reset line 118b permits the computer to reset the latch.

Advantageously, circuit 68 also includes a low duty cycle pulse generator 122 that also feeds into OR gate 116. In a preferred embodiment, a pulse having a 5 millisecond (ms) duration is generated at a 1 Hz repetition rate. When the laser 16 is in its zero or low intensity state, as it would be on power-up of analyzer 10 and as it would be after a drop in the detected Rayleigh scattering component below the threshold, each pulse from generator 122 causes the laser to momentarily (for the duration of the pulse) provide the higher output intensity. The pulses are kept short enough, and the duty cycle small enough, to keep the light emitted from probe 32 or even from connector pair 22 below the safety limits for the human eye and for explosive atmosphere environments. When system integrity returns to analyzer 10, the Rayleigh backscatter signal will return to line 66 during one of the pulses, causing circuit 114 to turn "ON", thereby establishing normal analyzer operation.

Still another input to OR gate 116 is a manual override pushbutton 124. When activated, pushbutton 124 forces laser 16 to the high output intensity. This capability is provided for troubleshooting purposes.

Figure 8:
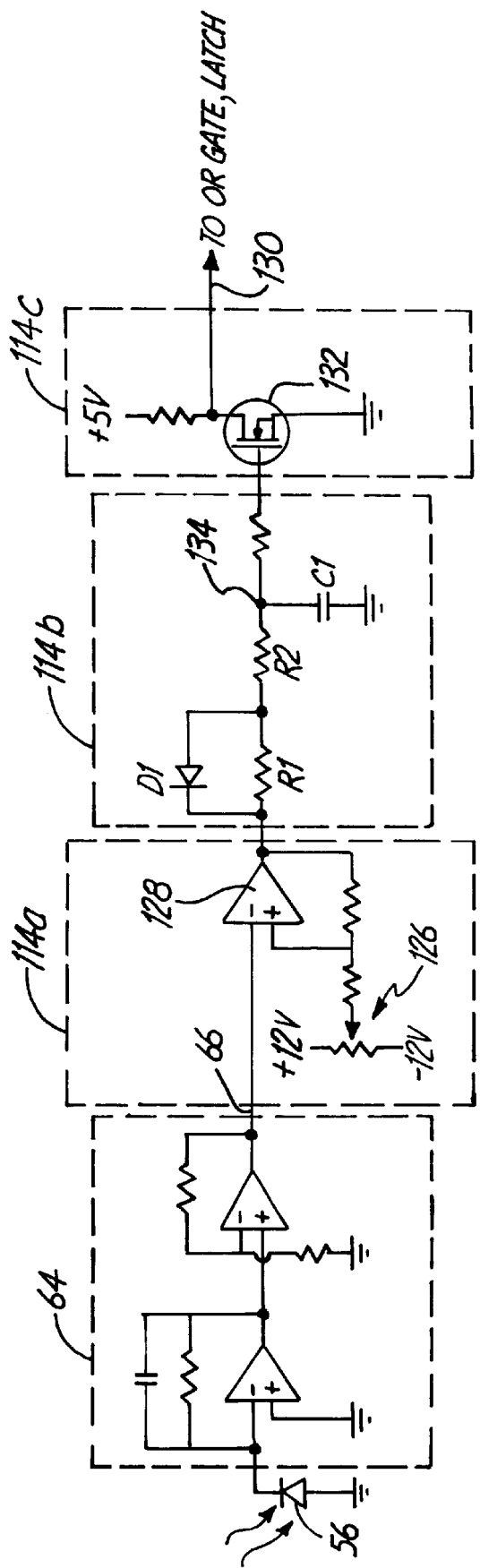
FIG. 8 is a schematic of a comparator/asymmetric discriminator circuit depicted as a block in FIG. 7.

Turning now to FIG. 8, the asymmetric transient discrimination feature of comparator/asymmetric discriminator circuit 114 will be described. The amplifier 64 is shown in more detail as a first stage transimpedance amplifier and a second stage amplifier with gain. The circuit 114 is shown as three circuits 114a, 114b, 114c connected in series. Circuit 114a, configured as shown, performs the comparator function described previously. Adjustment of potentiometer 126 adjusts the electric potential at the noninverting input of operational amplifier 128, which electric potential functions as the threshold referred to previously, against which the amplified detector output on line 66 is compared. Since operational amplifier 128 is wired as a comparator, it has essentially a digital output. This digital output changes state very rapidly every time the signal on line 66 crosses the threshold potential at the noninverting input of op amp 128. Ignoring circuit 114b for the moment, if circuit 114a was directly connected to circuit 114c, the circuit 114 output on line 130 would respond equally as rapidly to positive-going and negative-going changes in the line 66 signal as it crossed the threshold. However, as is apparent from the wiring of FET transistor 132 in circuit 114c, the polarity of the signal on line 130 is opposite that of the signal at the output of op amp 128.

Circuit 114b, however, discriminates between positive-going and negative-going transitions. During normal analyzer operation, with a Rayleigh scattering component above the threshold level, the output of op amp 128 is LO, the potential at node 134 is LO, capacitor C1 is not charged, and transistor 132 is off. If the Rayleigh scattering component suddenly drops below the threshold level, the output of op amp 128 immediately goes HI. Diode D1 is reverse biased (nonconducting), and the combination of resistors R1, R2, and capacitor C1 delay the turn-on of transistor 132. The delay ("τ") is proportional to (R1+R2)*C1. If the Rayleigh scattering component stays below the threshold level for at least the delay time τ, transistor 132 will turn on, causing the laser 16 to shut down. If however the detected Rayleigh component returns to a level above the threshold level before time τ has elapsed, op amp 128 output will immediately go LO, diode D1 will be forward biased (conducting), and capacitor C1 will discharge rapidly through only resistor R2. Preferably, the value of R1 is much greater than R2. In a preferred embodiment R1=200 kΩ, R2=10 kΩ, and C1=10 picofarads. Preferred delay times τ are in the range of about 0 to 44 ms, and are preferably programmable by computer 14 (e.g. by a computer-controlled switch and one or more resistors in circuit 114b that changes the effective resistance in parallel with diode D1).

In this manner, circuit 114b discriminates between a transitory loss in the detected Rayleigh scattering component and a transitory appearance of such component.

Figure 9:
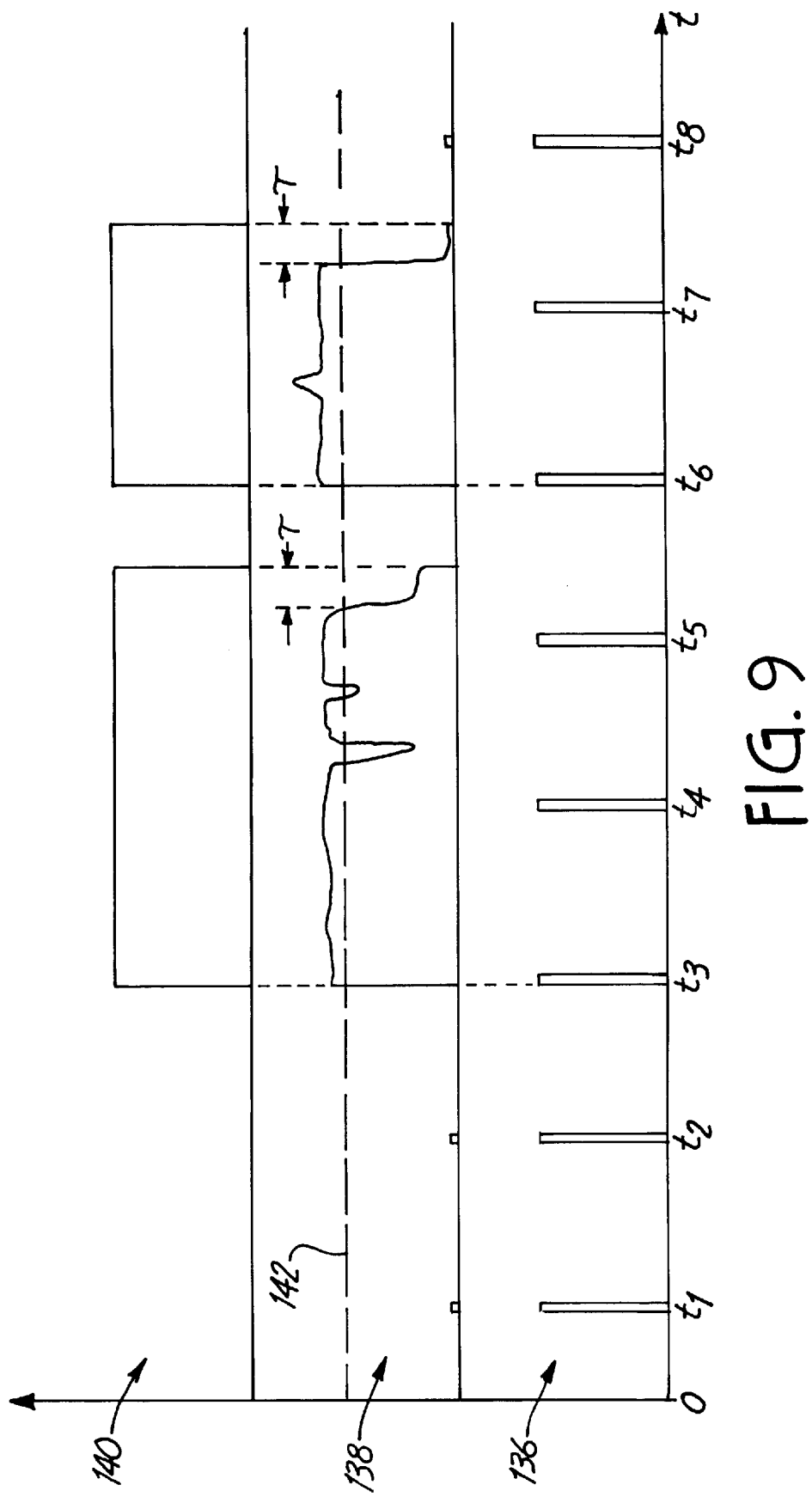
FIG. 9 is a timeline showing signals at different points in the signal conditioning circuit of FIG. 7.

FIG. 9 depicts the output of pulse generator 122, the amplified detector output on line 66, and the output of circuit 114 as waveforms 136, 138, 140 respectively. Broken line 142 represents the threshold level set in circuit 114. At time t=0, the analyzer is powered up, the laser is off, and the probe is withdrawn from the specimen. At times $t_1$ and $t_2$, the pulse generator pulses the laser on, but only a very low Rayleigh scattering component is detected since the probe is not contacting the specimen. Waveform 140 therefore remains off. Between times $t_2$ and $t_3$, the probe is inserted into the specimen, so that at the next pulse of waveform 136 at time $t_3$, a Rayleigh scattering component above the threshold is produced in waveform 138, and circuit 114 (waveform 140) rapidly responds. Between time $t_4$ and $t_5$, small bubbles passing through detection zone 54 cause transitory dips in waveform 142 below threshold 142. The duration of such dips is less than τ, so the waveform 140 remains unchanged. Between time $t_5$ and $t_6$, a larger bubble passes through detection zone 54, causing a dip in signal 138 with a duration longer than τ, whereupon waveform 140 drops to zero. By the time $t_6$, the large bubble has passed zone 54 and the pulse of waveform 136 brings back the Rayleigh scattering component in waveform 138 and the output of circuit 114. A transitory increase in waveform 138 between $t_6$ and $t_7$ has no effect on waveform 140, since waveform 138 stays above threshold 142 during that time. Between time $t_7$ and $t_8$, an interruption such as a fiber break, fiber disconnection, or probe withdrawal occurs. Waveform 138 responds immediately to the interruption, while waveform 140 responds after the delay time τ.

Although the present invention has been described with reference to preferred embodiments, workers skilled in the art will recognize that changes may be made in form and detail without departing from the spirit and scope of the invention. For example, analog circuits disclosed in the preferred embodiment can be replaced with equivalent digital circuits, e.g., DSP filters.

What is claimed is:

1. A method of fabricating a fiber optic probe, comprising:
   providing a probe terminus having a bore and a metal coating;
   providing a plurality of metal-coated fibers having proximal and distal ends;
   positioning the distal ends of the plurality of fibers inside the bore;
   placing a braze material on the probe terminus proximate the bore; and
   heating the probe terminus, the fiber distal ends, and the braze material in a vacuum oven to a temperature sufficient to melt the braze material, thereby causing the braze material to wick between the fibers inside the bore.

2. The method of claim 1, further comprising:
   connecting a probe body to the probe terminus;
   holding the proximal end of one of the plurality of fibers in a first connector, holding the proximal end of a second of the plurality of fibers in a second connector, and holding the proximal end of the remaining plurality of fibers together in a third connector; and
   fixing the first, second, and third connectors to the probe body.

3. The method of claim 1, further comprising:
   prior to the heating step, applying an anti-wicking agent to the plurality of fibers in a zone proximate the distal ends.

4. The method of claim 1, wherein the metal coating on the probe terminus is limited to a vicinity in and around the bore.

5. The method of claim 1, wherein the metal coating on the probe terminus comprises gold and the plurality of metal-coated fibers have a gold coating.

6. The method of claim 5, wherein the braze material is a binary metal alloy.

7. The method of claim 6, wherein the binary metal alloy includes silver and copper.

8. A probe for in situ spectroscopic analysis, comprising:
   a probe body having a distal end and a proximal end;
   a first optical fiber extending from the proximal end to the distal end; and
   a temperature sensor disposed in the probe body proximate the distal end.

9. The probe of claim 8, further comprising:
   a first fiber optic connector disposed at the proximal end and holding the first optical fiber.

10. The probe of claim 9, further comprising:

a second connector coupled to the temperature sensor and carried by the probe body at the proximal end.

11. The probe of claim 8, further comprising:

a second optical fiber extending from the proximal end to the distal end; and a second fiber optic connector disposed at the proximal end and holding the second optical fiber.

12. The probe of claim 11, further comprising:

a third optical fiber extending from the proximal to the distal end; and a third fiber optic connector disposed at the proximal end and holding the third optical fiber.

13. The probe of claim 10, wherein the temperature sensor includes a thermocouple.

* * * * *

UNITED STATES PATENT AND TRADEMARK OFFICE
CERTIFICATE OF CORRECTION

PATENT NO. : 6,244,753 B1
DATED : June 12, 2001
INVENTOR(S) : O'Connor et al.

Page 1 of 1

It is certified that error appears in the above-identified patent and that said Letters Patent is hereby corrected as shown below:

Title page,
Item [73], Assignee, change "Rosemount Analytical, Inc." with -- Rosemount Analytical Inc. --.
Item [57], ABSTRACT,
Line 6, replace "so" with -- to --.

Signed and Sealed this

Twelfth Day of February, 2002

Attest:

JAMES E. ROGAN
*Attesting Officer*          *Director of the United States Patent and Trademark Office*